United States Patent [19]
Stevens

[11] Patent Number: 5,484,731
[45] Date of Patent: Jan. 16, 1996

[54] MULTIWELL IN-VITRO FERTILIZATION PLATE

[75] Inventor: Timothy A. Stevens, Madison, N.J.

[73] Assignee: Becton, Dickinson and Company, Franklin Lakes, N.J.

[21] Appl. No.: 67,640

[22] Filed: May 26, 1993

[51] Int. Cl.⁶ .................................................. C12M 1/20
[52] U.S. Cl. ................... 435/305.3; 206/558; 220/345; 220/374; 422/102; 435/284.1
[58] Field of Search .................................... 435/297–301; 422/102; 206/569, 558; 220/345, 346, 351, 367, 374

[56] References Cited

U.S. PATENT DOCUMENTS

| | | | |
|---|---|---|---|
| 1,975,245 | 10/1934 | Zackheim | 422/102 |
| 3,097,070 | 7/1963 | Aldrich et al. | 422/102 |
| 3,406,821 | 10/1968 | Weissberg | 220/345 |
| 3,563,859 | 2/1971 | Fink | 435/301 |
| 3,655,515 | 4/1972 | Noorlander | 435/301 |
| 3,741,877 | 6/1973 | Shafus | 435/297 |
| 3,883,398 | 5/1975 | Ono | 435/298 |
| 4,012,288 | 3/1977 | Lyman et al. | 435/301 |
| 4,062,445 | 12/1977 | Moe | 220/346 |
| 4,296,862 | 10/1981 | Armentrout et al. | 220/374 |
| 4,431,307 | 2/1984 | Suovaniemi | 422/102 |
| 4,495,289 | 1/1985 | Lyman et al. | 435/301 |
| 4,657,867 | 4/1987 | Guhl et al. | 435/301 |
| 4,682,891 | 7/1987 | de Macario et al. | 422/102 |
| 4,786,601 | 11/1988 | Rothenberg | 435/301 |
| 5,000,923 | 3/1991 | Coville et al. | 422/102 |
| 5,021,218 | 6/1991 | Davis et al. | 422/102 |
| 5,042,683 | 8/1991 | Shaw et al. | 220/345 |
| 5,084,246 | 1/1992 | Lyman et al. | 435/301 |

FOREIGN PATENT DOCUMENTS

| | | |
|---|---|---|
| 0239450 | 9/1987 | European Pat. Off. . |
| WO9106624 | 5/1991 | WIPO . |

Primary Examiner—James C. Housel
Assistant Examiner—Jan M. Ludlow
Attorney, Agent, or Firm—Arthur D. Dawson

[57] ABSTRACT

A plate assembly for useful for in vitro fertilization procuedures such as receiving ova and for forming, evaluating, holding, manipulating and culturing embryos includes a base with an apportioned top surface and a sidewall. The top surface has a plurality of open wells embedded therein for receiving ova to be cultured. The wells are substantially cylindrical and have substantially flat closed bottoms to facilitate microscopic examination of the well contents. The assembly includes a removable lid for covering the top surface of the base. The lid is preferably divided into sections comparable to the top surface portions of the base. Each lid section may be separately slidably moved between a closed position where the lid covers a comparable portion of the top surface and an open position where the top surface is uncovered. The lid has projections which interact with grooves in the base in a cam/cam follower relationship to allow slidable movement of the lid sections between the closed and the open positions while retaining the lid sections to the base. The inside surface of the lid and the base top surface each have elements which interact when the lid is in the closed position to form a tortuous path for gas interchange between the wells and the outside environment, thus substantially preventing microbial contamination of the wells when the lid is closed.

17 Claims, 2 Drawing Sheets

MULTIWELL IN-VITRO FERTILIZATION PLATE

FIELD OF THE INVENTION

The present invention relates to tissue culture apparatus and more particularly to a plate apparatus useful in forming, holding, manipulating and growing mammalian embryos.

DESCRIPTION OF RELATED INFORMATION

Formation and growth of mammalian embryos has become increasing important. The advances in understanding of the mechanisms of ovum generation coupled with advances in ultrasound imaging and microsurgical techniques have fostered a tremendous increase in formation and growth of mammalian embryos, both for domestic animals and especially for human embryos as in vitro fertilization (IVF) techniques have been perfected.

In a human IVF procedure generally the female is treated with hormones to stimulate maturation of multiple ova. These ova are then surgically recovered by microsurgical techniques directly from the ovary. The recovered ova are then placed into a suitable vessel and exposed to sperm collected from the male for fertilization. After fertilization occurs, the fertilized ovum is allowed to grow to a multi-celled embryo, then recovered and returned to the female, where implantation of the embryo on the wall of the uterus is expected to occur, resulting, from that time forward, in a normal pregnancy.

In order to generate a suitable embryo for implantation by the IVF procedure briefly outlined above, practitioners must be highly skilled in many manipulative procedures as well as interpretation of laboratory results. Initially, a determination needs to be made of the dosage of hormones to be administered to the female. This determination may involve specialized blood tests, ultrasound imaging and laparoscopic procedures. During the hormone dosage phase, blood hormone levels are determined and ultrasound evaluation of the ovaries is often practiced. The collection of the ova is another specialized procedure involving ultrasound imaging and microsurgery. Once the ova are collected, careful microscale manipulations and optical microscopic evaluation of individual ovum, sperm, fertilized ovum and embryo are part of the process to generate an embryo suitable for implantation. The implantation phase again may involve ultrasound imaging and microsurgical techniques. In each phase, specialized equipment plays an important role in the success of the procedure.

Specialized equipment has been developed to assist practitioners in every phase of the IVF process. An important part of the process is the phase where the collected ova are placed into a laboratory vessel for the fertilization and growth. Initially, practitioners used ordinary glass petri dishes (hence the "in vitro" [glass] terminology). Specialized laboratory ware such as that disclosed in international Patent Application No. WO 91/06624 by Lyman et al. is available. Lyman et al. teach a dish for IVF procedures. The dish has a single fertilization well concentrically surrounded by a second well for containing a humidification fluid. The humidification well with the fluid helps to maintain humidity in the fertilization well when the lid, similar to an ordinary petri dish lid, is in place on the dish.

European Publication No. 0 239 450 by Cassou teaches a carousel apparatus for IVF. The Cassou apparatus is complex, holding many dishes and includes a glove box for facilitating the handling the dishes and a microscope for observing the contents of the dishes during manipulations.

There are also multiwell dishes intended for tissue culture. U.S. Pat. No. 3,883,398 to Ono teaches a multiwell microculture slide chamber for simultaneous growing of a plurality of mono-layer cell cultures on a slide which can then be separated for microscopic study of the culture.

All of these devices have been developed to assist practitioners in the microculture of tissue and embryos. All provide improvements over the standard "petri" dish originally used for the culture procedures, but there is still a need for an easily manipulated multiwell assembly particularly intended for receiving ovum, formation of fertilized ovum, manipulating and culturing the fertilized ovum into an embryo suitable for implantation. The present invention is a plate assembly particularly addressing the needs of practitioners in the IVF procedures for generation of mammalian embryos.

SUMMARY OF THE INVENTION

A plate assembly useful for in vitro fertilization procedures includes a base with an apportioned top surface and a sidewall. The top surface has a plurality of open wells embedded therein for receiving ova and for forming holding, manipulating and culturing embryos. The wells preferably are substantially cylindrical and have substantially flat closed bottoms to facilitate microscopic examination of the embryo growing within the well. The assembly includes a removable lid for covering the top surface of the base. Preferably, the lid is divided into sections comparable to the top surface portions of the base. Each lid section may be separately slidably moved between a closed position where the lid covers the top surface portion and an open position which uncovers the top surface portion. The wells in the top surface have open tops with a raised lip projecting above the top surface. The lid inside surface preferably has a plurality of raised rings corresponding in number to the number of wells in the base. The rings are preferably positioned and sized so that when the lid is in the closed position, the rings form a concentric barrier adjacent and outside the lips on the wells. When the lid is closed, the barrier provides a tortuous path for gas interchange with the well, substantially retains condensate from the well, and substantially prevents microbial contamination of the wells. The top surface portions have a perimeter defined by a continuous raised shoulder. The lid section inside surface has a perimeter substantially equivalent to the base portion perimeter. The lid surface perimeter has a raised bead defining it. The raised bead is positioned so that when the lid section is in the closed position and the rings are adjacent to the lips on the wells, the raised shoulder is positioned substantially adjacent the raised bead forming a tortuous path for gas interchange.

In one embodiment, the assembly is substantially square with four substantially equal cylindrical wells embedded in the surface. The wells have substantially flat transparent bottoms for facilitating microscopic evaluation of embryos contained in the wells. In this embodiment the lid has two substantially equal sections. The base has a plurality of grooves in the sidewall section and the lid inside surface has projections fit within the grooves in a cam/cam follower relationship in which the projections are in a first position when the lid section is in the closed position and in a second position when the lid is slidably moved to the open position. When the lid is in the second position, the projections positioned in the groove serve to retain the lid section to the assembly. A further attribute of the embodiment of the present invention is an extension to the base sidewall below the portion covered by the lid. The extension is sized and shaped to aid manipulation of the assembly and has a surface finish to receive identification marketing.

DETAILED DESCRIPTION

Figure 1:
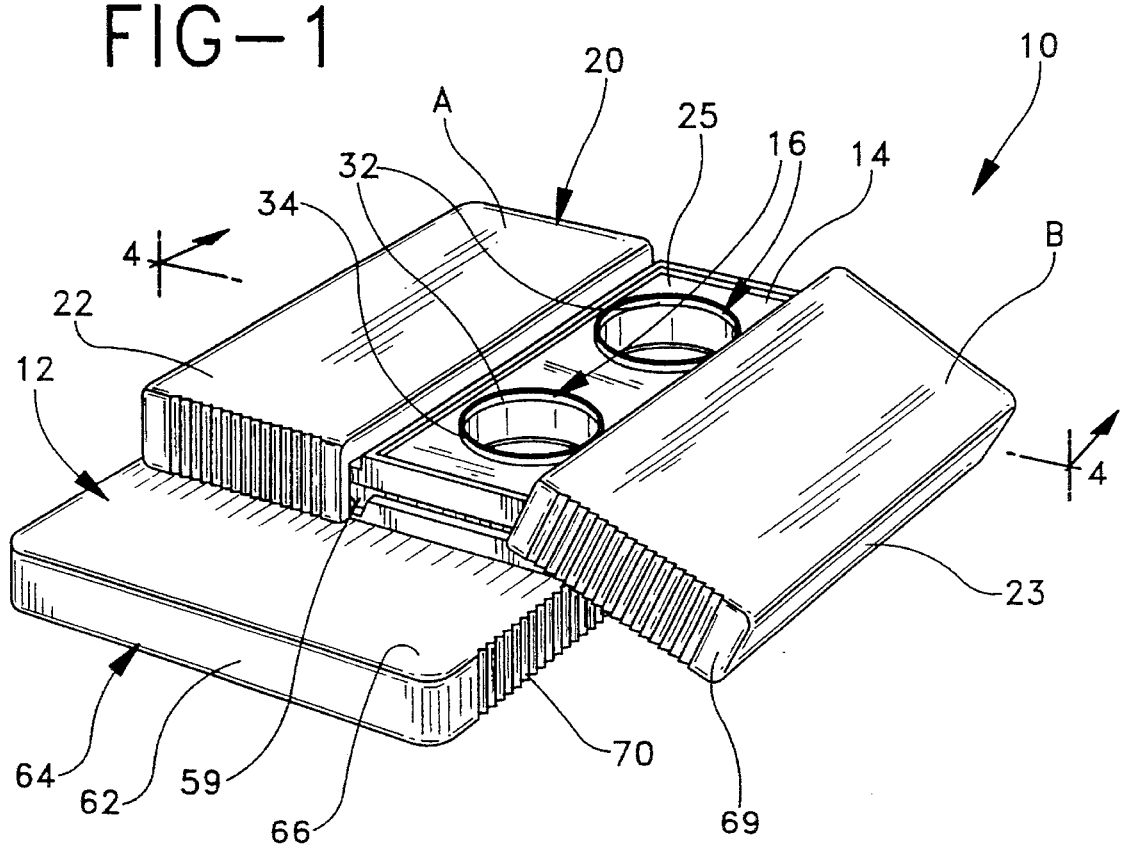
FIG. 1 is a perspective view of a preferred embodiment of a plate assembly of the present invention.

While this invention is satisfied by embodiments in many different forms, there is shown in the drawings and will herein be described in detail, a preferred embodiment of the invention with the understanding that the present disclosure is to be considered exemplary of the principles of the invention and is not intended to limit the invention to the embodiments illustrated. The scope of the invention will be measured by the appended claims and their equivalents.

FIGS. 1–4 show a preferred embodiment of a plate assembly 10 for receiving ova, and for forming, evaluating, manipulating and culturing embryos. Assembly 10 includes a base 12 with an apportioned top surface 14 having two top surface portions 24 and 25. One skilled in the art will recognize that for certain applications a plurality of top surface portions may be desireable. Top surface 14 has a plurality of wells 16 embedded therein. Base 12 further includes a sidewall 17. Wells 16 are substantially cylindrical and have substantially flat transparent bottoms 18. The substantially flat transparent bottoms facilitate microscopic examination of the contents of the wells through the bottoms of the wells so that an embryo present in the well may be examined and manipulated under a microscope.

Assembly 10 preferably includes a lid 20 divided into sections 22 and 23 which are comparable to top surface portions 24 and 25 respectively. Each lid section may be separately slidably moved between a closed position A, e.g. wherein comparable top surface portion 24 is covered by lid section 22, and an open position B, e.g., wherein comparable top surface portion 25 is exposed by sliding lid section 23 to open position B.

Wells 16 have open tops 32 and raised lips 34 which preferably are continuous and project above top surface 14. Lid 20 has inside surfaces 36 and 37 on portions 22 and 23 respectively with a plurality of raised rings 38 projecting therefrom. Rings 38 preferably correspond in number to the number of wells and are preferably positioned and sized so that when lid sections 22 and 23 are in the closed position as demonstrated by A and respectively covering top surface portions 24 and 25, rings 38 form a substantially concentric barrier 40 adjacent and outside lips 34 on the wells. Barrier 40 provides a first tortuous path 42 for gas interchange with wells 16 and substantially retains any condensation formed on lid surface 36 from the contents of wells.

It has been recognized since the early work of Pasteur, that microorganisms have mass and, since they have no means for locomotion in air, move in straight lines. Thus a tortuous path such as path 42 of the present invention, in addition to allowing for gas interchange with wells 16, substantially provides a barrier to passage of microorganisms into the well when lid 20 is in place.

Preferred top surface portions 24 and 25 of apportioned top surface 14 have perimeters 44 and 45 respectively. Perimeters 44 and 45 respectively include raised shoulders 46 and 47. Inside surfaces 36 and 37 of lid sections 22 and 23 respectively have raised beads 50 and 51. Beads 50 and 51 substantially correspond to raised shoulders 46 arid 47 respectively, so that when lid sections 22 and 23 are in the closed position and rings 38 are adjacent lips 34, shoulders 46 and 47 are adjacent beads 50 and 51 respectively, forming a second tortuous path 52. Second tortuous path 52 allows gas interchange between surface 14 and the outside environment while substantially preventing microbial contamination of surface 14 when the lid is in the closed position.

Preferably, beads 50 and 51 include a plurality of standoffs 54 for contacting shoulders 46 and 47 and maintaining a clearance between beads 50 and 51 and shoulders 46 and 47.

Figure 2:
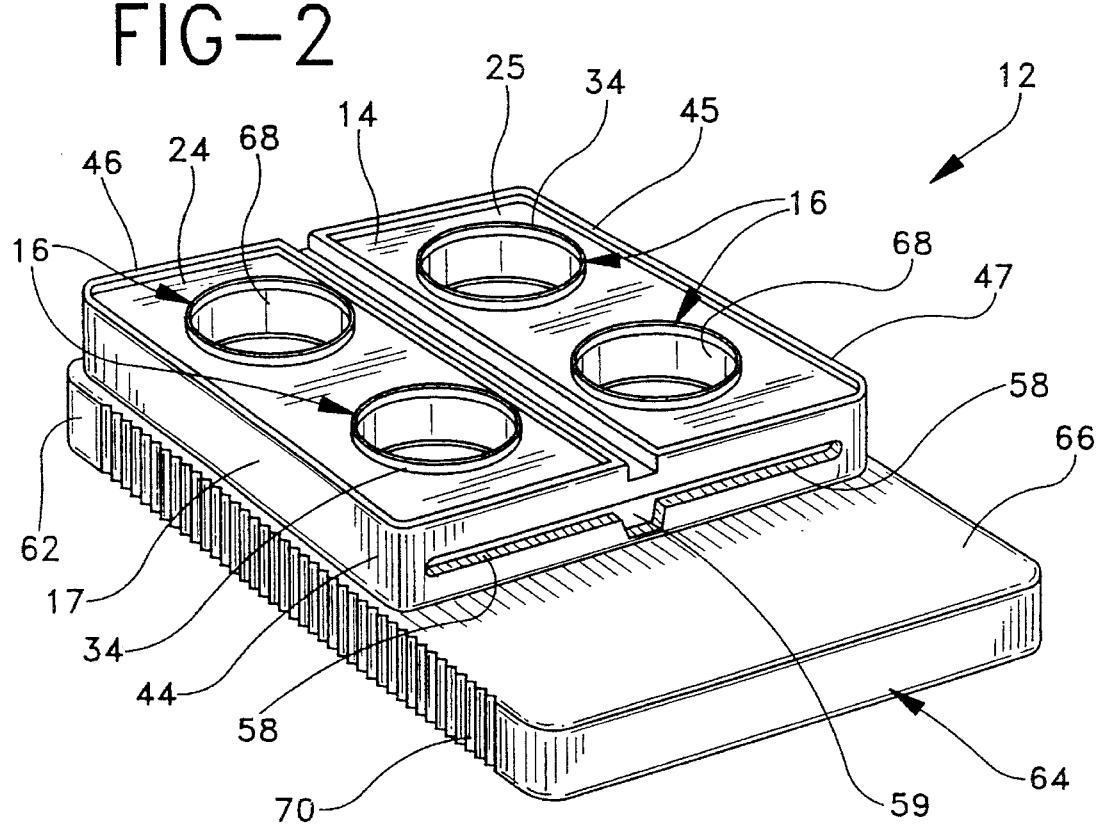
FIG. 2 is a perspective view of a preferred embodiment of the base with the lid removed.
Figure 3:
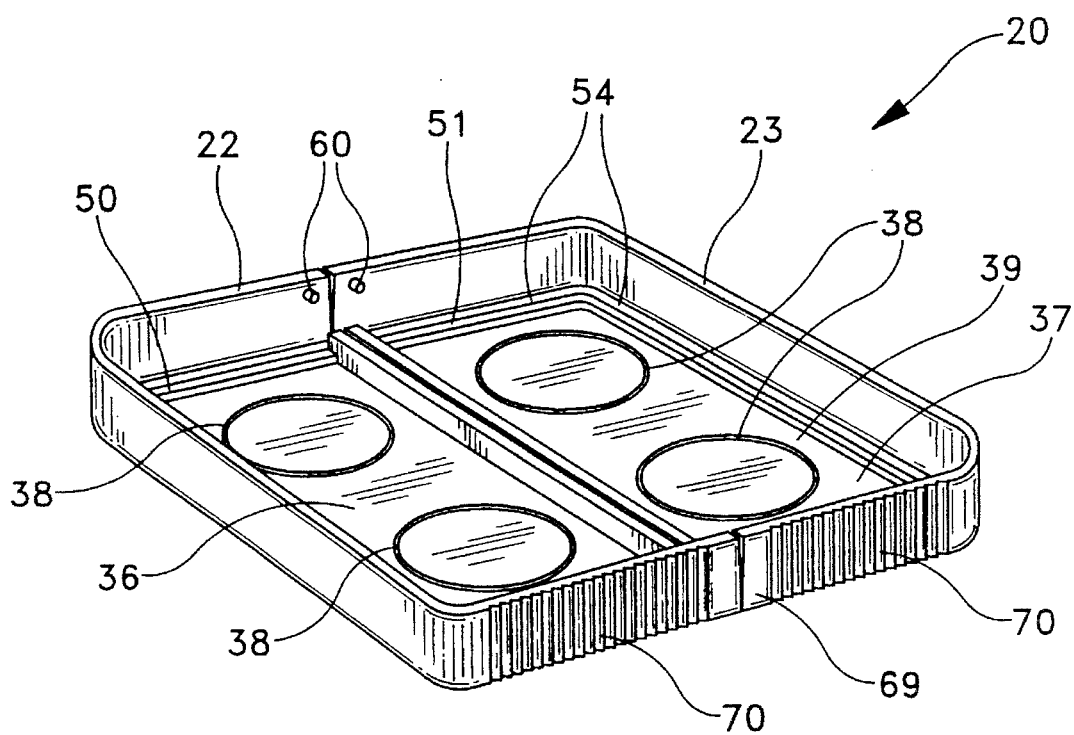
FIG. 3 is perspective view of a preferred embodiment of the inside surface of the lid sections.
Figure 4:
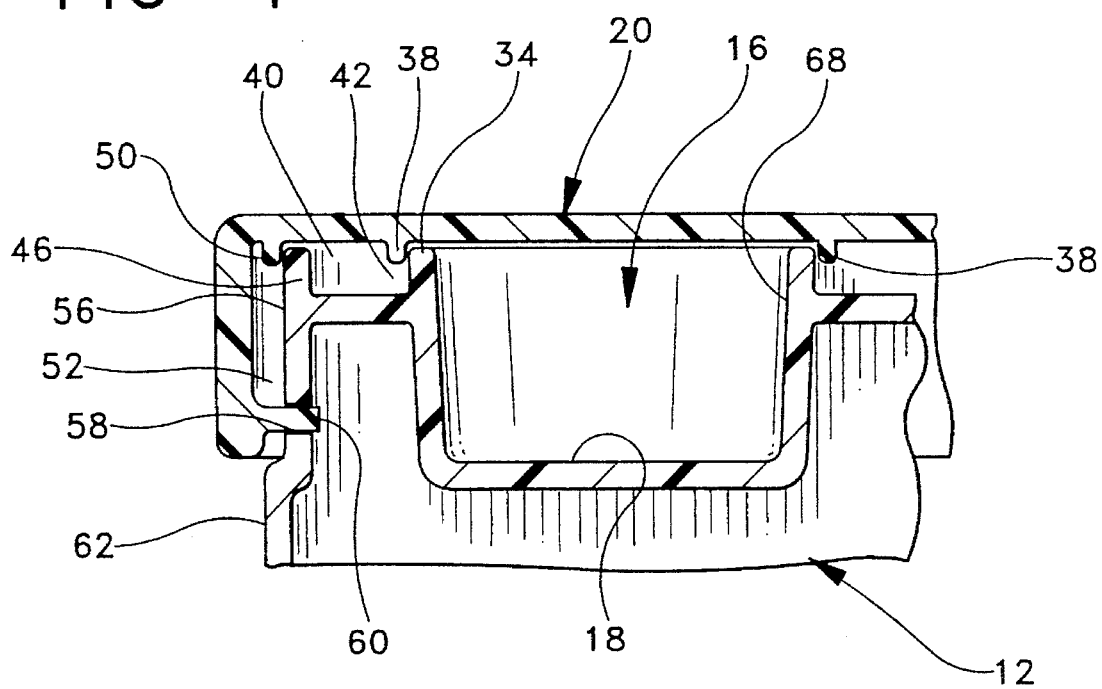
FIG. 4 is a partial sectional detail of the embodiment of FIG. 1 shown along line 4, 4.

As shown in FIGS. 1–3, assembly 10 preferably is substantially square having top surface 14 divided into two substantially equal rectangular portions 24 and 25. Each top surface portion preferably has two substantially cylindrical wells 16 embedded therein.

The preferred embodiment of assembly 10 further includes lid 20 with sections 22 and 23 being extended to cover a first portion 56 of sidewall 17. First sidewall portion 56 preferably includes a plurality of grooves 58. Lid sections 22 and 23 preferably include inward projections 60 on inside surfaces 36 and 37. Inward projections 60 are positioned and sized to fit in grooves 58 in a cam/cam follower relationship so that when lid sections 22 and 23 are positioned in the closed position covering top surface portions 24 and 25 respectively, projections 60 are in a first position in grooves 58. When lid sections 22 and 23 are in the open position, uncovering top surface portions 24 and 25, projections 60 are in a second position in grooves 58, so as to releasably retain lid sections 22 and 23 to base 12. Grooves 58 preferably further include detents 59 for releasably retaining projections 60 when lid 20 is closed.

Base 12 preferably further includes a second sidewall portion 62 not covered by lid 20. At least a part of sidewall portion 62 includes an extension 64 having a surface 66. Extension 64 is sized and shaped to facilitate manipulation of assembly 10 and preferably surface 66 includes a surface finish suitable for receiving identification markings.

One skilled in the art of making laboratory ware will recognize that assembly 10 may be formed from a variety of materials. Desirably the assembly may be formed from a plastic resin sheet by vacuum forming and the like, and preferably assembly 10 is injection molded from a plastic resin having substantially no extractable components. It is further preferred that the resin and the method used for forming assembly 10 provide an optically transparent structure, particularly the flat well bottom, for facilitating observation of the contents of the wells without removal of the lid. Polystyrene, polycarbonate and the like have been shown to be suitable for injection molding of assembly 10.

Wells 16 have an inside surface 68 to which various surface treatments such as plasma, surface oxidation, coatings and the like which are known to facilitate the attachment of growing cells, may be applied. Preferably any treatment applied to surface 68 does not reduce the optical transmission properties of well bottom 18.

The outside surface of base 12 not covered by the lid in the closed position, as well as an outside lid surface 69, preferably include sections having raised knurling 70 for facilitating gripping and manipulating the assembly. The particular design and location of the knurling may be selected to be compatible with the assembly forming process and particular user requirements.

Assembly 10 may be individually packaged using materials which provide a barrier to the passage of microorganisms, then subjected to an environment which renders any microorganisms present inside the package non-viable. Alternatively assembly 10 may be bulk packaged and sterilized, with the preferred incorporation of the tortuous paths in the assembly serving to substantially prevent microbial contamination of the top surface and wells until the lid is removed. Another embodiment is to incorporate one or more units of assembly 10 into a specialized procedure kit for IVF.

A description of how an IVF procedure using assembly 10 of the present invention is conducted is as follows. A female patient is evaluated and administered a hormone dosage sufficient to hyperstimulate the ovaries. The hyperstimulated ovaries bring multiple ova to maturation, with the ova then collected using ultrasound imaging and microsurgical techniques. The ova (generally numbering 5 to 9) and the associated fluid, called cumulus, are transferred to a suitable vessel, e.g. a polystyrene tube such as a Falcon Labware 2003, available from Becton, Dickinson and Company, Franklin Lakes, N.J. Individual ovum are then be transferred to the assembly of the present invention. The preferred procedure calls for one ovum each to the rear most wells (i.e., 2 ovum per assembly) for cleaning and examination. After cleaning and examination, each ovum is transferred to the front well (adjacent to the extension) of the assembly with about 70 to 100 microliters of specialized growth media. Sperm, previously collected from the male, is added to the well to fertilize the ovum, and the cover is closed. The well is microscopically examined to determine if the fertilization is successful. Following a successful fertilization, the fertilized ovum is allowed to grow and microscopically observed every 6–8 hours. The preferred present invention, with the separately slidable lid sections, allows opening a well for examination and manipulation of the contents while leaving the wells under the other section covered, thereby substantially preventing microbial contamination and maintaining a controlled atmosphere over the growing embryo. When the embryo has reached sufficient maturity for implantation, it is harvested from the well and transferred, using microsurgical techniques, to the female's fallopian tube from where it is expected to implant on the wall of the uterus. Once an implantation occurs, the result is be the beginning of a normal gestation.

The plate assembly of the present invention provides practitioners of IVF procedures with a dependable, easy-to-use vessel for receiving, cleaning and evaluating ova, fertilizing the ovum, determining if the fertilization was successful, and culturing the fertilized ovum into an embryo suitable for implantation.

What is claimed is:

1. A plate assembly useful for in vitro fertilization procedures comprising:

a base having a top surface divided into top surface portions and a sidewall, said top surface having a plurality of open wells therein, said wells having an inside surface for receiving ova to be cultured into embryos, said wells having substantially flat transparent closed bottoms for facilitating microscopic examination therethrough; and a removable lid for covering said top surface and at least a portion of said sidewall of said base, said lid being divided into sections, wherein each section of said lid is separately slidably movable between a closed position wherein said each lid section covers said each top surface portion and an open position uncovering said each top surface portion.

2. The assembly of claim 1 wherein said base further includes said wells being substantially cylindrical and having open tops each with a raised lip projecting above said top surface; and wherein said lid further includes an inside surface having a plurality of raised rings projecting therefrom, said rings corresponding in number to said plurality of said wells in said base portion, said rings being positioned and sized so that when said each lid section is in said closed position, said rings form a substantially concentric barrier adjacent and outside said lips on said wells, thereby providing a tortuous path for gas interchange with said wells.

3. The assembly of claim 2 wherein said base top surface portions have a perimeter defined by a continuous raised shoulder, said lid sections each having a perimeter, said lid sections inside surface each having a raised bead defining said perimeter, said bead being sized and positioned so that when said lid section is in said closed position and said rings are adjacent to said lips, said raised shoulder is positioned substantially adjacent said raised bead, thereby forming a tortuous path for gas interchange and substantially preventing microbial contamination.

4. The assembly of claim 3 wherein each bead further includes a plurality of standoffs projecting therefrom for contacting said shoulder, thereby maintaining a clearance between said shoulder and said bead when said lid sections are in said closed position.

5. The assembly of claim 1 wherein said base top surface is substantially square, having two substantially equal portions, each portion having two substantially equal cylindrical wells substantially symmetrically therein.

6. The assembly of claim 5 wherein said sidewall has a plurality of grooves therein, and said lid sections having inward projections placed and sized to fit in said grooves in a cam/cam follower relationship so that when said lid sections are positioned for covering said wells, said projections are in a first position in said grooves, and when said lid sections are slidably moved to uncover said top surface, said projections are in a second position in said grooves, thereby retaining said lid sections on said base.

7. The assembly of claim 6 wherein said base further includes an extension located on a second portion of said sidewall not covered by said lid sections when lid sections are in said closed position, said extension being sized and shaped for aiding manipulation of said assembly, and said extension having a surface for receiving identification marking.

8. The assembly of claim 7 formed from a plastic resin.

9. The assembly of claim 8 wherein said inside surface of said wells has a treatment selected from the group consisting of plasma treatment and surface oxidation for facilitating cell attachment and growth.

10. A plate assembly for receiving ova, for forming, evaluating, holding, manipulating and culturing embryos comprising:

a base having a sidewall and a substantially square top surface having four substantially equal generally cylindrical wells therein, said wells having an inside surface and closed bottoms, said bottoms being substantially flat and transparent for observing therethrough, each well having an open top and a lip projecting above said top surface, said top surface being divided into two substantially equal portions, said portions each having two wells and a perimeter defined by a raised shoulder; and a removable lid for covering said top surface of said base and a first portion of said sidewall, said lid being divided into two substantially equal sections, each section separately slidably movable between a closed position wherein said one portion of said top surface is covered and an open position wherein said one portion of said top surface is uncovered, said lid sections each having an interior surface substantially corresponding to said top surface portions, said surfaces of said lid sections each having thereon two substantially circular raised rings and a perimeter defined by a raised bead, said bead and said rings being positioned and sized so that when said lid sections cover said top surface, said rings are outside and adjacent said lips and said bead is adjacent said raised shoulder forming a tortuous path at said perimeter and at said lip of said wells for gas interchange and substantially preventing microbial contamination.

11. The assembly of claim 10 wherein said sidewall has a plurality of grooves in said first portion of said sidewall, and said lid sections each have projections, said projections being placed and sized to fit within and slidably move within said grooves in a cam/cam follower relationship when said lid sections are slidably moved between said closed position and said open position, thereby substantially retaining said lid section on said base.

12. The assembly of claim 11 wherein said base further includes an extension located on a second portion of said sidewall, said second portion not being covered by said lid when said lid is in said closed position, said extension being shaped and sized for aiding manipulation of said assembly and having a surface for receiving identification marking.

13. The assembly of claim 11 wherein said grooves have detents for releasably retaining said projections when said lid sections are in said closed position.

14. The assembly of claim 11 wherein said lid sections have an outside surface, at least a portion of said lid sections outside surface having raised knurling for facilitating gripping and slidably moving said sections.

15. The assembly of claim 11 wherein at least a portion of said second portion of said sidewall of said base includes raised knurling for facilitating gripping and slidably moving said lid sections.

16. A packaged plate assembly useful for in vitro fertilization procedures comprising:

a sealed package substantially resistant to the passage of microorganisms having therewithin a plate assembly including a base having a top surface divided into top surface portions and a sidewall, said top surface having a plurality of open wells therein, said wells having an inside surface for receiving ova to be cultured into embryos, said wells having substantially flat transparent closed bottoms for facilitating microscopic examination therethrough; and a removable lid for covering said top surface and at least a portion at said sidewall, of said base, said lid being divided into sections, wherein each section of said lid is separately slidably moved between a closed position wherein said lid section covers said each top surface portion and an open position uncovering said each top surface portion.

17. The assembly of claim 11 formed from a plastic resin.

* * * * *